United States Patent [19]

Krause

[11] 3,956,382
[45] May 11, 1976

[54] PROCESS FOR THE PRODUCTION OF ETHER POLYCARBOXYLIC ACIDS

[75] Inventor: Horst-Jürgen Krause, Dusseldorf, Germany

[73] Assignee: Henkel & Cie G.m.b.H., Dusseldorf, Germany

[22] Filed: Oct. 21, 1974

[21] Appl. No.: 516,209

[30] Foreign Application Priority Data

Oct. 24, 1973   Germany............................ 2353176

[52] U.S. Cl. ........................... 260/535 P; 260/484 P
[51] Int. Cl.$^2$......................................... C07C 59/22
[58] Field of Search...................... 260/535 P, 484 P

[56] References Cited
FOREIGN PATENTS OR APPLICATIONS 902,359   8/1962   United Kingdom............. 260/484 P Primary Examiner—Anton H. Sutto
Assistant Examiner—P. J. Killos
Attorney, Agent, or Firm—Hammond & Littell

[57] ABSTRACT

A process for the production of ether polycarboxylic acids comprising reacting alkali metal salts of ether carboxylic acids with carbon dioxide in the presence of (1) an alkaline compound selected from the group of alkali metal carbonates, bicarbonates and hydroxides and (2) optionally, heavy metal catalysts and inert diluents at temperatures of 200°C to 350°C under pressure, acidify the resulting alkali metal salt of an ether polycarboxylic acid and recovering said ether polycarboxylic acid.

12 Claims, No Drawings

PROCESS FOR THE PRODUCTION OF ETHER POLYCARBOXYLIC ACIDS

It is known that ether polycarboxylic acids, as well as their alkali salts, are good sequestering agents, particularly for the hardness-formers of water. But the practical use of these products was heretofore prevented by the fact that there was no economical production method for them. There is therefore a need for a method which permits the production of these compounds on a large technical scale.

U.S. Pat. No. 3,359,310 describes a method for the production of the potassium salt of malonic acid or malonic acid itself by the carboxylation of potassium acetate with carbon dioxide under pressure in the presence of potassium carbonate and a heavy metal catalyst at temperatures of about 300°C. However, one skilled in the art would not expect this reaction with its arduous conditions of pressure and temperature to be applied to labile ether carboxylic acids because, according to general knowledge, ethers are very easily cleaved by the action of metals at higher temperatures.

An object of the present invention is the development of a process for the production of ether polycarboxylic acids consisting essentially of reacting an inorganic alkali metal salt of an ether carboxylic acid having the formula $$R - O - CHR' - COOH$$

wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal compound selected from the group consisting of carbonates, bicarbonates and hydroxides and (2) from 0% to 30% by weight, based on the weight of the reaction mixture of a heavy metal catalyst, a finely-divided inert diluent and an inert liquid diluent, at a temperature of between 200°C and 350°C under a pressure of at least 10 atmospheres gauge, for a time sufficient to effect carboxylation, and recovering said ether polycarboxylic acids.

This and other objects of the invention will become more apparent as the description thereof proceeds.

The above objects were achieved and the problems of the prior art were overcome in that an ether carboxylic acid of the formula $$R - O - CHR' - COOH$$

where R denotes an alkyl with 1 to 22 carbon atoms, which can be straight-chain or branch-chain, and substituted by hydroxyl or carboxyl groups or interrupted by oxygen atoms, and where R' denotes hydrogen or a lower alkyl with 1 to 4 carbon atoms, is reacted in the form of its alkali metal salts in the presence of alkali metal carbonates, alkali metal hydrogen carbonates or alkali metal hydroxides and, optionally, heavy metal catalysts, as well as inert diluents, with carbon dioxide at temperatures of 200°C to 350°C, preferably 250°C to 300°C under pressure, preferably above 200 atmospheres gauge, and that the alkali metal salt of the ether polycarboxylic acids formed is transferred if necessary, in known manner into the free acids to give the desired ether polycarboxylic acids.

More particularly, the invention relates to a process for the production of ether polycarboxylic acids consisting of reacting an alkali metal salt of an ether carboxylic acid having the formula $$R - O - CHR' - COOH$$

wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal compound selected from the group consisting of carbonates, bicarbonates and hydroxides and (2) from 0% to 30% by weight, based on the weight of the reaction mixture of a heavy metal catalyst, a finely-divided inert diluent and an inert liquid diluent, at a temperature of between 200°C and 350°C under a pressure of at least 10 atmospheres gauge, for a time sufficient to effect carboxylation, and recovering said ether polycarboxylic acids.

As indicated above, U.S. Pat. No. 3,359,310 gives a process for the production of potassium malonate or malonic acid by carboxylation of potassium acetate with carbon dioxide under pressure in the presence of potassium carbonate and heavy metal catalysts at temperatures of about 300°C. Application of this reaction with its adverse conditions of pressure and temperature to the labile ether carboxylic acids would seem out of the question for the man skilled in the art since, according to general knowledge, ethers are very easily split during metallization at higher temperatures.

It was completely unexpected, therefore, to find according to the invention that the alkli metal salts of the ethers of α-hydroxycarboxylic acids of the above-mentioned general formula could be carboxylated with a high yield in the presence of alkali metal carbonates, alkali metal hydrogen carbonates or alkali metal hydroxides and carbon dioxide under pressure, while maintaining certain temperature conditions. The carboxylation is effected on the carbon atom in the α-position to the carboxyl group. With ether carboxylic acids which contain several carboxyl groups in the molecule, carboxylation is possible on all carbon atoms which are in α-position to carboxyl groups or on only one carbon atom which is in the adjacent or α-position to a carboxyl group. The degree of reaction of the carboxylation depends to a great extent on the selected temperature conditions.

The carboxylation of the ether carboxylic acids to be reacted takes place in the presence of alkali metal carbonate according to the following reaction:

$$R-O-CH_2-COOM + M_2CO_3 + CO_2 \rightarrow$$
$$R-O-CH\begin{smallmatrix}COOM\\COOM\end{smallmatrix} + MHCO_3 \quad (M = Na \text{ or } K)$$

Where a dicarboxylic acid such as diglycolic acid is employed the reaction is as follows:

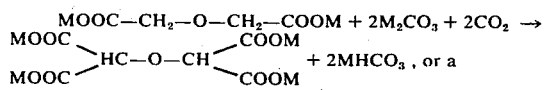

mixture of ether polycarboxylic acids are produced as follows:

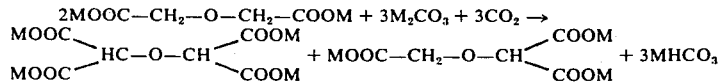

The alkali metal carbonate serves in this reaction as a deprotonizing agent and at the same time to neutralize and stabilize the carboxyl group formed. In order to obtain good yields of ether polycarboxylic acids, it is therfore advisable to use at least the stoichiometric amount of alkali metal carbonate for the carboxyl groups present in the starting material. Preferably, however, a certain excess of alkali metal carbonate is used. The same holds true for the carboxylation of the ether carboxylates in the presence of alkali metal hydrogen carbonate (alkali metal bicarbonate) or alkali metal hydroxide.

All alkali metal salts of ether carboxylic acids which meet the conditions of the above-mentioned general formula can be used as starting materials for the production of the other polycarboxylic acids according to the invention. Examples of such compounds suitable for carboxylation are the alkali metal salts of alkylglycolic acids such as methylglycolic acid, ethylglycolic acid, butylglycolic acid, laurylglycolic acid, alkyl-$C_{12-18}$-glycolic acid, also oxaalkylglycolic acids or polyoxaalkylglycolic acids such as etherification products of glycolic acids with ethylene-oxide (EO) addition products on alcohols, particularly on fatty alcohols, such as the lauryl alcohol + 2 EO ether of glycolic acid, myristic alcohol + 3 EO ether of glycolic acid, stearyl alcohol + 6 EO ether of glycolic acid; furthermore, carboxyl substituted alkylglycolic acids such as diglycolic acid, the lactic acid ether of glycolic acid, and carboxyl substituted oxaalkyl glycolic acids such as ethylene-bis-glycolic acid. Primarily, the potassium and sodium salts are employed as the alkali metal salts. The alkali metal salts of the ether carboxylic acids used as starting materials for the method according to the invention should be present if possible in dry form, since it is advisable to avoid the presence of large amounts of water during the reaction. Preferably, the reaction is conducted under substantially anhydrous conditions.

The production of the alkali metal salts of the ether carboxylic acids used as starting materials in the present method can be effected according to methods known from the literature, and is not the subject of the invention.

The most suitable from among the alkali metal salts of the ether carboxylic acids are the potassium salts in combination with potassium carbonate. But all other combinations, like the sodium salts with potassium carbonate, potassium hydrogen carbonate or potassium hydroxide, potassium salts with sodium carbonate, sodium hydrogen carbonate or sodium hydroxide, and sodium salts with sodium carbonate, sodium hydrogen carbonate or sodium hydroxide, as well as mixtures of the alkali metal carbonates, alkali hydrogen carbonates or alkali hydroxides, can also be used.

The alkali metal salts of the ether carboxylic acids are reacted according to the invention in the presence of alkali metal carbonates, alkali hydrogen carbonates or alkali hydroxides with carbon dioxide under pressure. The pressure can vary within very wide limits, but should be at least 10 atmospheres gauge. The desired reaction can already be obtained with a relatively low overpressure, e.g. about 10 to 50 atmospheres. But in order to obtain good yields, it is generally desirable to utilize a carbon dioxide pressure of more than 200 atmospheres at the reaction temperature. The upper limit of the pressure is determined by the available apparatus. It can be 1000 to 2000 atmospheres or more. The pressure can be produced by corresponding pumps or compressors. In laboratory tests, liquid or solid carbon dioxide can be filled into the cooled and evacuated reaction vessel. The carbon dioxide can be recirculated, just like the other ingredients.

The reaction temperature is very critical in the present method in order to avoid decomposition of the ether carboxylic acids. In order to obtain a sufficiently rapid reaction for technical purposes, temperatures above 200°C are required. The reaction temperature, however, should not exceed 350°C if possible, unless decomposition is prevented at the same time by very high pressures. A preferred temperature range is between 250°C and 300°C. The optimum temperature depends on the desired degree of carboxylation as well as on the nature of the ether carboxylic acids used and the type of alkali metals used.

The reaction takes only a short time; but larger batches may take several hours, because of the required time for heating and cooling. Care must be taken that local overheating, which can lead to decomposition, is avoided during the heating step. For this reason, too rapid heating should be avoided. In general, a reaction time of 1 to 3 hours will be sufficient.

As it can be seen from the above reaction equation, the execution of the reaction requires the presence of acid-binding agents, which neutralize and stabilize the newly formed carboxyl groups. This is achieved with the alkali metal carbonates, alkali metal hydrogen carbonates and alkali metal hydroxides, preferably potassium carbonate. The acid-binding substances should be present in at least stoichiometric amounts, as mentioned above. Preferably, however, a certain excess is used.

Water and oxygen should be excluded, as far as possible in the present method, as in all metallo-organic synthesis, if good yields are to be obtained. If necessary, water-binding substances can be added.

The water of reaction formed with the use of alkali metal hydrogen carbonates and alkali metal hydroxides can be removed by replacing the supernatant gas in the course of the reaction continuously or intermittently by dry carbon dioxide.

The reaction according to the invention is catalytically influenced by a number of heavy metals or heavy metal compounds. Suitable metals are, for example, iron, bismuth, zinc, nickel, copper, cadmium, titanium and chromium, which can be used as such or in the form of their oxides or salts with inorganic or organic acids, such as carbonates, bicarbonates, halides, acetates, sulfates, formates, exalates or higher fatty acid salts. Of particular advantage for the reaction according to the invention is the use of iron or zinc powder as a catalyst.

The amount of catalyst can vary within wide limits of 0 to 15% by weight, and is preferably 0.5% to 5% by weight, based on the reaction mixture, when employed.

Furthermore, it was found advantageous to add to the reaction mixture, inert substances with a large surface area, such as kieselguhr, finely divided silica, powdered carbon black, finely divided aluminum oxide, in order to improve the mechanical-physical properties of the mixture and to prevent the possible formation of lumps. The technical realization of the method is thus made considerably easier. The amount of inert additives can vary within very wide limits and is determined by the design of the apparatus used. Ordinarily, from 0 to 20% by weight, based on the weight of the reaction mixture of the finely-divided inert diluents, are employed.

Finally, the reaction can also be carried out in the presence of inert liquid diluents, such an amount of diluent is preferably so selected that a pumpable mixture is obtained. Ordinarily, from 0 to 30% by weight, based on the weight of the reaction mixture, of the inert liquid diluents are employed.

The method can be carried out continuously or intermittently. Thus, for example, it is possible to work according to the fluidized bed method. In an intermittent operation it is advisable to use rolling autoclaves or autoclaves equipped with a stirrer as the reaction vessels.

The reaction mixture can be worked up by dissolving the entire reaction mixture in water and filtering off the insoluble components, like the catalyst and inert additives. The ether polycarboxylic acids can be obtained from the aqueous solution by acidification with mineral acids or by treatment with a cation exchanger in acid form and subsequent preparation according to the known methods.

The ether polycarboxylic acids obtained can be used with very good results as sequestering agents. In many cases, particularly for use as sequestering agents for the hardness of the water in detergents and cleaning agents, it is not necessary to produce the ether carboxylic acids in the free acid form, their alkali metal salts can be used with just as good results. In addition, the product mixtures obtained in the method according to the invention can also be used, after they have been separated from the catalyst and inert substances.

The following examples will illustrate the invention without limiting it, however, to these examples.

EXAMPLES

In the following examples, the procedure was as follows, unless indicated otherwise. The dried anhydrous starting materials were finely ground in a ball mill and heated in a high-pressure autoclave of 500 ml capacity under carbon-dioxide pressure.

The "initial pressure" was the carbon dioxide pressure in the autoclave before commencing the heating. This pressure was adjusted in each case at 50°C, in view of the critical temperature of carbon dioxide. The "end pressure" was the maximum pressure observed at the corresponding reaction temperature.

In many cases the autoclave was provided with a glass insert or partial lining. This is indicated in the respective tests.

For the working up of the reaction mixture, the crude product was dissolved in water and filtered hot. After cooling, the filtrate was mixed with stirring with a particulated cation exchange resin in acid form in order to acidify the product, whereby the carbon dioxide could escape without foaming. Subsequently the ion-exchange resin was filtered off and the aqueous solution of the ether polycarboxylic acids was conducted through a fresh cation exchange resin column in the acid form, in order to transform it completely into the free acid. The eluate was evaporated under vacuum until dry. The total yield of the ether polycarboxylic acids obtained this way corresponds to the analytical composition of the reaction mixtures.

The analytical composition of the ether polycarboxylic acids obtained was determined by gas chromatography of the methyl esters after esterification of the acids with diazomethane. The usual analytical data were determined from the pure single fractions obtained by distillation or gas chromatography.

In the following tables of the following examples, the individual abbreviations have the following meanings:

| | |
|---|---|
| init. pressure | = the initial carbon dioxide pressure in atmospheres measured at 50°C |
| E-pressure | = the end carbon dioxide pressure at the respective reaction temperature |
| temp. | = the reaction temp. in °C, measured in vapor area. |
| comp. TC % | = the percent composition of total carboxylic acids |
| DG | = diglycolic acid |
| CMT | = carboxymethyl ether of tartronic acid (2-oxa-propane-1,1,3-tricarboxylic acid) |
| DT | = ditartronic acid (2-oxa-propane-1,1,3,3-tetracarboxylic acid) |
| DOA | = dodecyloxy-acetic acid |
| MA + B | = malonic acid + byproducts |
| DOM | = dodecyloxy-malonic acid |
| E-b-G | = ethylene-bis-glycolic acid |
| EDAM | = ethanedioxy-1-acetic acid-2-malonic acid |
| E-b-T | = ethylene-bis-tartronic acid |
| M-d-G | = methyl-diglycolic acid |
| OBTC | = 2-oxabutane-1,1,3-tricarboxylic acid |
| B | = byproducts |

EXAMPLES 1 to 11 (glass insert) and 12 to 18

Batch: 21.0 gm of the potassium salt of diglycolic acid (0.1 mol)
78.0 gm of anhydrous potassium carbonate (0.56 mol)
8.0 gm of finely-divided silica or without additive
1.0 gm of catalyst or without catalyst The heating time to the reaction temperature is indicated in hours at the respective temperature.

The results of the tests are compiled in the following Table I.

TABLE I

| example | init. press. | E- press. | temp. °C duration-hrs. | catalyst | additive | comp. TC% |
|---|---|---|---|---|---|---|
| 1 | 300 | 900 | 200 3 | Fe-powder 1 gm | silica 8 gm | 100DG |
| 2 | 250 | 790 | 250 3 | Fe-powder 1 gm | silica 8 gm | 96.3DG;3.7CMT |
| 3 | 245 | 740 | 260 3 | Fe-powder 1 gm | silica 8 gm | 54.3DG;36.4CMT; 2.4 DT;6.9MA+B |
| 4 | 230 | 780 | 270 3 | Fe-powder 1 gm | silica 8 gm | 15.0DG;53.1CMT; 19.2DT;12.7MA+B |
| 5 | 230 | 800 | 275 3 | Fe-powder 1 gm | silica 8 gm | 10.3DG;50.0CMT; 19.7DT;20.0MA+B |
| 6 | 220 | 735 | 280 3 | Fe-powder 1 gm | silica 8 gm | 6.8DG;39.8CMT; 9.4DT;44.0 MA+B |
| 7 | 220 | 910 | 290 3 | Fe-powder 1 gm | silica 8 gm | 23.0 DG;17.1 CMT; 6.7DT;53.2 MA+B |
| 8 | 230 | 1050 | 300 3 | Fe-powder 1 gm | silica 8 gm | 39.2DG;5.3 CMT; 8.1 DT; 47.4 MA+B |
| 9 | 85 | 240 | 275 3 | Fe-powder 1 gm | silica 8 gm | 33.9 DG; 55.4 CMT; 6.5 DT; 4.2 MA+B |
| 10 | 100 | 345 | 275 3 | Fe-powder 1 gm | silica 8 gm | 18.6 DG; 54.8 CMT; 13.6 DT; 13.0 MA+B |
| 11 | 230 | 800 | 275 3 | Zn-powder 1 gm | silica 8 gm | 12.9DG;44.4 CMT; 10.6 DT; 32.1 MA+B |
| 12 | 250 | 1050 | 265 3 | Fe-powder 1 gm | silica 8 gm | 58.3 DG; 28.6 CMT; 10.2 DT; 2.9 MA+B |
| 13 | 240 | 750 | 270 1 | Fe-powder 1 gm | silica 8 gm | 40.4DG;44.0 CMT; 2.4 DT; 13.2 MA+B |
| 14 | 240 | 800 | 270 3 | without | silica | 11.5 DG; 46.9 CMT; 12.6 DT; 29.0 MA+B |
| 15 | 250 | 1020 | 270 3 | Fe-powder 1 gm | without | 9.0 DG; 46.5 CMT; 19.1 DT; 25.4 MA+B |
| 16 | 240 | 850 | 270 3 | Cu-powder 1 gm | silica 8 gm | 43.9 DG; 35.2 CMT; 20.9 MA+B |
| 17 | 240 | 850 | 270 3 | Cu-Zn-pair 1 gm (powder) | silica 6 gm | 15.9 DG; 43.9 CMT; 4.2 DT; 29.0 MA+B |
| 18 | 240 | 880 | 270 3 | CdO 1 gm | silica 4 gm | 18.7 DG; 49.6 CMT; 3.2 DT; 22.2 MA+B |

EXAMPLE 19

Batch: 21.0 gm of the potassium salt of diglycolic acid (0.1 mol)
60.0 gm of anhydrous sodium carbonate (0.56 mol)
8.0 gm of Aerosil
1.0 gm of iron powder The results of the tests are compiled in Table II.

EXAMPLE 20

Batch: 17.8 gm of the sodium salt of diglycolic acid (0.1 mol)
60.0 gm of anhydrous sodium carbonate (0.56 mol)
8.0 gm of Aerosil
1.0 gm of iron powder The results of the tests are compiled in Table II.

TABLE II

| Example | init. press. | E- press. | temp. °C duration-hrs. | comp. TC% |
|---|---|---|---|---|
| 19 | 250 | 960 | 270 3 | 65.6 DG; 33.1 CMT; 0.8 DT; 0.5 MA+B |
| 10 | 240 | 960 | 270 3 | 90.4 DG; 9.6 CMT |

EXAMPLE 21

Batch: 19.8 gm of the potassium salt of ethylene-bis-glycolic acid (0.078 mol)
86.0 gm of anhydrous potassium carbonate (0.62 mol)
8.0 gm of Aerosil
1.0 gm of iron powder

| init. press. | E- press. | temp. °C duration-hrs. | comp. TC% |
|---|---|---|---|
| 240 | 1050 | 270 3 | 11.9 EbG; 35.0 EDAM 52.9 EbT; 0.2 B |

EXAMPLE 22

Batch: 22.4 gm of the potassium salt of methyl-diglycolic acid (0.1 mol) (carboxymethyl-lactic acid)
82.9 gm of anhydrous potassium carbonate (0.6 mol)
8.0 gm of Aerosil
1.0 gm of iron powder

| init. press. | E- press. | temp. °C duration-hrs. | comp. TC% |
|---|---|---|---|
| 240 | 800 | 270 3 | 29.5% M-d-G; 52.3 OBTC. 18.2% B |

EXAMPLES 23 and 24

Batch: 14.1 gm of the potassium salt of dodecyl acetic acid (0.05 mol)
10.5 gm of anhydrous potassium carbonate (0.075 mol)
2.0 gm of Aerosil

| Example | init. press. | E- press. | temp. °O duration-hrs. | comp. TC% |
|---|---|---|---|---|
| 23 | 260 | 830 | 290 3 | 84.0 DOA; 14.8 DOM; 0.3B |
| 24 | 270 | 1040 | 270 3 | 73.8 DOA; 26.0 DOM |

EXAMPLE 25

Batch: 21.0 gm of the dipotassium salt of diglycolic acid (0.1 mol)
29.0 gm of anhydrous potassium carbonate -continued

| init. press. | E- press. | temp. °C duration-hrs. | comp. TC% |
|---|---|---|---|
| 270 | 1050 | 270 3 | 26.2 DG; 50.3 CMT; 14.0 DT; 9.5 MA+B |

EXAMPLE 26

Batch: 21.0 gm of the dipotassium salt of diglycolic acid (0.1 mol)
12.0 gm of potassium hydrogen carbonate (0.12 mol)
4.0 gm of Aerosil The mixture was first heated for 2 hours to 270°C. Then the carbon dioxide in the autoclave was removed and replaced by fresh carbon dioxide up to a pressure of 150 atmospheres at 255°C. The mixture was then heated again for 1 hour to 270°C.

| init. press. | E- press. | temp. °C duration-hrs. | comp. TC% |
|---|---|---|---|
| 270 (50°C) | 980 | 270; 2 | 59.3 DG; 36.1 CMT |
| 150 (260°C) | 190 | 270; 1 | 3.8 DT; 0.8 B |

EXAMPLE 27

BATCH: 21.0 gm of the dipotassium salt of diglycolic acid (0.1 mol)
30.0 gm of potassium hydrogen carbonate (0.3 mol)
4.0 gm of Aerosil The mixture was heated for a total of 3 hours at 270°C. The original carbon dioxide was replaced as in Example 26, after 2 hours by fresh carbon dioxide.

| init. press. | E- press. | temp. °C duration-hrs. | comp. TC% |
|---|---|---|---|
| 270 (50°C) | 880 | 270; 2 | 48.5 DG; 45.8 CMT |
| 150 (260°C) | 190 | 270; 1 | 5.1 DT; 0.6 B |

EXAMPLE 28

Batch: 21.0 gm of the potassium salt of diglycolic acid (0.1 mol)
8.3 gm of potassium hydroxide 88% (0.15 mol)
5.0 gm of Aerosil As in Example 26, the carbon dioxide contained in the autoclave was replaced after 2 hours at 270°C by fresh carbon dioxide.

| init. press. | E- press. | temp. °C duration-hrs. | comp. TC% |
|---|---|---|---|
| 270 (50°C) | 1030 | 270; 2 | 67.1 DG; 31.2 CMT |
| 150 (260°C) | 190 | 270; 1 | 1.2 DT; 0.5 B |

EXAMPLE 29

Batch: 17.8 gm of the disodium salt of diglycolic acid (0.1 mol)
8.3 gm of anhydrous potassium carbonate
4.0 gm of Aerosil The example was carried out in analogy to Example 26.

| init. press. | E- press. | temp. °C duration-hrs. | comp. TC% |
|---|---|---|---|
| 270 (50°C) | 950 | 270; 2 | 83.3 DG; 15.0 CMT |
| 150 (260°C) | 170 | 270; 1 | 2.7 B |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A process for the production of ether polycarboxylic acids consisting essentially of reacting an alkali metal salt of an ether carboxylic acid having the formula $$R - O - CHR' - COOH$$

wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an inorganic alkali metal compound selected from the group consisting of carbonates, bicarbonates and hydroxides and (2) from 0% to 30% by weight, based on the weight of the reaction mixture of a heavy metal catalyst, a finely-divided inert diluent and an inert liquid diluent, at a temperature of between 200°C and 350°C under a pressure of at least 10 atmospheres gauge, for a time sufficient to effect carboxylation, and recovering said ether polycarboxylic acids.

2. The method of claim 1 wherein said alkali metal salt of an ether carboxylic acid is the potassium salt.

3. The method of claim 1 wherein said alkali metal compound is potassium carbonate.

4. The method of claim 1 wherein said alkali metal salt of an ether carboxylic acid is the potassium salt and said alkali metal compound is potassium carbonate.

5. The method of claim 1 wherein said reaction is conducted under substantially anhydrous conditions in the substantial absence of oxygen.

6. The method of claim 1 wherein from 0.5% to 5% by weight of iron powder is employed as a heavy metal catalyst.

7. The method of claim 1 wherein from 0.5% to 5% by weight of zinc powder is employed as a heavy metal catalyst.

8. The method of claim 1 wherein up to 30% by weight of a finely-divided inert diluent is employed.

9. The method of claim 1 wherein R is dodecyl and R' is hydrogen.

10. The method of claim 1 wherein R is carboxymethyl and R' is hydrogen.

11. The method of claim 1 wherein R is carboxymethyloxaethyl and R' is hydrogen.

12. The method of claim 1 wherein R is carboxymethyl and R' is methyl.

* * * * *